(12) United States Patent
Peterson et al.

(10) Patent No.: US 11,517,358 B2
(45) Date of Patent: Dec. 6, 2022

(54) INTERFRAGMENTARY GUIDE AND PLATE SYSTEM

(71) Applicant: Arthrex, Inc., Naples, FL (US)

(72) Inventors: Scott Peterson, Naples, FL (US);
Mihaela Morar, Naples, FL (US);
Zack Day, Naples, FL (US); Troy Watson, Henderson, NV (US)

(73) Assignee: Arthrex, Inc., Naples, FL (US)

( * ) Notice: Subject to any disclaimer, the term of this patent is extended or adjusted under 35 U.S.C. 154(b) by 550 days.

(21) Appl. No.: 16/590,419

(22) Filed: Oct. 2, 2019

(65) Prior Publication Data
US 2021/0100594 A1   Apr. 8, 2021

(51) Int. Cl.
| | | |
|---|---|---|
| *A61B 17/72* | (2006.01) | |
| *A61B 17/80* | (2006.01) | |
| *A61B 17/88* | (2006.01) | |
| *A61B 17/00* | (2006.01) | |
| *A61B 17/68* | (2006.01) | |
| *A61B 17/90* | (2006.01) | |

(52) U.S. Cl.
CPC ...... *A61B 17/7291* (2013.01); *A61B 17/8057* (2013.01); *A61B 17/8897* (2013.01); *A61B 17/90* (2021.08); *A61B 2017/00407* (2013.01); *A61B 2017/681* (2013.01)

(58) Field of Classification Search
CPC ............ A61B 17/7291; A61B 17/1728; A61B 17/1717; A61B 17/1775; A61B 17/1782; A61B 17/1757; A61B 17/17; A61B 17/8897; A61B 17/80; A61B 17/90; A61B 2017/00407; A61B 2017/681
See application file for complete search history.

(56) References Cited

U.S. PATENT DOCUMENTS

| | | | |
|---|---|---|---|
| 7,316,687 B2 | 1/2008 | Aikins et al. | |
| 8,523,919 B2 | 9/2013 | Huebner et al. | |
| 8,652,180 B2 | 2/2014 | Federspiel et al. | |
| 9,011,457 B2 | 4/2015 | Grady, Jr. et al. | |
| 9,060,822 B2 * | 6/2015 | Lewis | A61B 17/8014 |
| 9,545,276 B2 | 1/2017 | Buchanan et al. | |

(Continued)

OTHER PUBLICATIONS

Paragon 28 Gorilla R3Con Plating System.
Paragon 28 Gorilla R3Con Plating System Surgical Technique Guide.

*Primary Examiner* — Eduardo C Robert
*Assistant Examiner* — Anna V. Little
(74) *Attorney, Agent, or Firm* — Carlson, Gaskey & Olds, P.C.

(57) ABSTRACT

A plating system includes a bone plate including an aperture. A locking member is receivable in the aperture to attach the bone plate to a joint. The plating system includes a guide including a body having a first end portion, a second end portion, an attachment portion attached to the bone plate, and a rotating portion including a sleeve to receive a drill or a guide wire. The first end portion of the body is rotationally connected to the attachment portion to pivot the body about a first axis to move the sleeve, and the rotating portion is rotationally connected to the second end portion of the body of the guide to pivot the rotating portion about a second axis to move the sleeve. The rotating portion translates along the second axis to move the sleeve, and the sleeve defines one of a plurality of trajectories.

19 Claims, 2 Drawing Sheets

(56) References Cited

U.S. PATENT DOCUMENTS

| | | |
|---|---|---|
| 9,907,562 B2 | 3/2018 | Dacosta et al. |
| 9,936,995 B2 | 4/2018 | Dacosta et al. |
| 10,201,358 B2 | 2/2019 | Seykora et al. |
| 10,258,351 B2 | 4/2019 | Biedermann |
| 2009/0088804 A1 | 4/2009 | Kyle et al. |
| 2009/0157077 A1 | 4/2009 | Larsen et al. |
| 2010/0063549 A1* | 3/2010 | Orbay .................. A61B 17/68 606/280 |
| 2013/0012945 A1 | 1/2013 | Chreene et al. |
| 2014/0180348 A1* | 6/2014 | Thoren ............. A61B 17/1728 606/86 R |
| 2015/0134011 A1 | 5/2015 | Medoff |
| 2015/0359580 A1* | 12/2015 | Dacosta ................ A61B 17/56 606/281 |
| 2016/0045238 A1 | 2/2016 | Bohay et al. |
| 2017/0156768 A1 | 6/2017 | Dresher et al. |
| 2017/0333102 A1* | 11/2017 | Peterson ............ A61B 17/8057 |
| 2018/0242987 A1* | 8/2018 | Lintula ............. A61B 17/1775 |
| 2018/0289402 A1 | 10/2018 | Lueth et al. |
| 2019/0133611 A1* | 5/2019 | Schreiber ............ A61B 17/808 |
| 2020/0337747 A1 | 10/2020 | Dresher et al. |

\* cited by examiner

INTERFRAGMENTARY GUIDE AND PLATE SYSTEM

BACKGROUND

This disclosure relates to an interfragmentary guide and plate system.

SUMMARY

An interfragmentary guide and plate system includes a plate and a guide. The plate is attached to a joint. The guide includes a sleeve that can receive a drill or a guide wire. The drill creates a passage in the joint that receives an interfragmentary screw.

Embodiments of the plating system disclosed herein include a bone plate attached to a joint with a plurality of screws. The plating system also includes a guide that includes a sleeve to receive a drill or guide wire. The guide includes a first portion pivotable about a first axis and a second portion pivotable about a second axis. The second portion vertically translates along the second axis. The pivoting and rotation position the sleeve in a desired position to receive the drill or guide wire, and the sleeve defines a plurality of screw trajectories. The drill forms a passage in the joint along one of the plurality of screw trajectories, and the passage receives an interfragmentary screw.

In an embodiment, a plating system includes a metatarsophalangeal (MTP) plate including an aperture and an opening. A locking member is receivable in the aperture to attach the MTP plate to an MTP joint. The plating system includes an MTP guide including a body, an attachment portion, and a rotating portion. The body includes a first end portion and a second end portion that has a passage that receives the rotating portion. The attachment portion is attached to the MTP plate and includes an arm having an end portion. The rotating portion includes at least one dimple and a sleeve to receive a drill or guide wire. The first end portion of the body and the end portion of the arm of the attachment portion are rotationally connected and define a ratcheting mechanism. The ratcheting mechanism allows for rotation of the body, and the body pivots about a first axis to move the sleeve. The rotating portion is rotationally connected to the second end portion of the body of the MTP guide, and the rotating portion pivots about a second axis to move the sleeve. The rotating portion also vertically translates along the second axis and relative to the second end portion of the body to move the sleeve. A sleeve longitudinal axis of the sleeve intersects and is perpendicular to the second axis. The body of the MTP guide includes another opening in communication with the passage of the body, and the another opening has an opening longitudinal axis that intersects and is substantially perpendicular to the second axis of the rotating portion. An another fastener is received in the another opening and spring biased to engage the at least one dimple of the rotating portion and prevent rotation and vertical translation of the rotating portion relative to the body. The attachment portion of the MTP guide is attached to the MTP plate by a fastener that is received in the opening of the MTP plate. One of the MTP plate and the MTP guide includes an alignment pin and the other of the MTP plate and the MTP guide includes a recess, and the alignment pin is received in the recess to prevent rotation of the MTP guide relative to the MTP plate.

In another embodiment, a plating system includes a bone plate including an aperture, and a locking member is receivable in the aperture to attach the bone plate to a joint. The plating system includes a guide including a body, an attachment portion, and a rotating portion. The body includes a first end portion and a second end portion. The attachment portion is attached to the bone plate, and the rotating portion includes a sleeve to receive a drill or guide wire. The first end portion of the body is rotationally connected to the attachment portion and pivots about a first axis to move the sleeve, the rotating portion is rotationally connected to the second end portion of the body of the guide and pivots about a second axis to move the sleeve, the rotating portion translates along the second axis to move the sleeve, and the sleeve defines one of a plurality of trajectories.

In another embodiment, a method for positioning a sleeve that receives a drill or guide wire includes rotating a body of a guide relative to an attachment portion of the guide to pivot the body about a first axis to move a sleeve of a rotating portion of the guide. The attachment portion of the guide is attached to a bone plate. The method includes rotating the rotating portion of the guide relative to the body of the guide to pivot the rotating portion about a second axis to move the sleeve of the rotating portion of the guide. The method includes translating the rotating portion along the second axis relative to the body of the guide to move the sleeve of the rotating portion. The method includes securing the rotating portion relative to the body to secure the sleeve of the rotating portion in a desired location relative to a joint.

BRIEF DESCRIPTION OF THE DRAWINGS

The various features and advantages will become apparent to those skilled in the art from the following detailed description of the currently preferred embodiment. The drawings that accompany the detailed description can be briefly described as follows.

DETAILED DESCRIPTION

Figure 1:
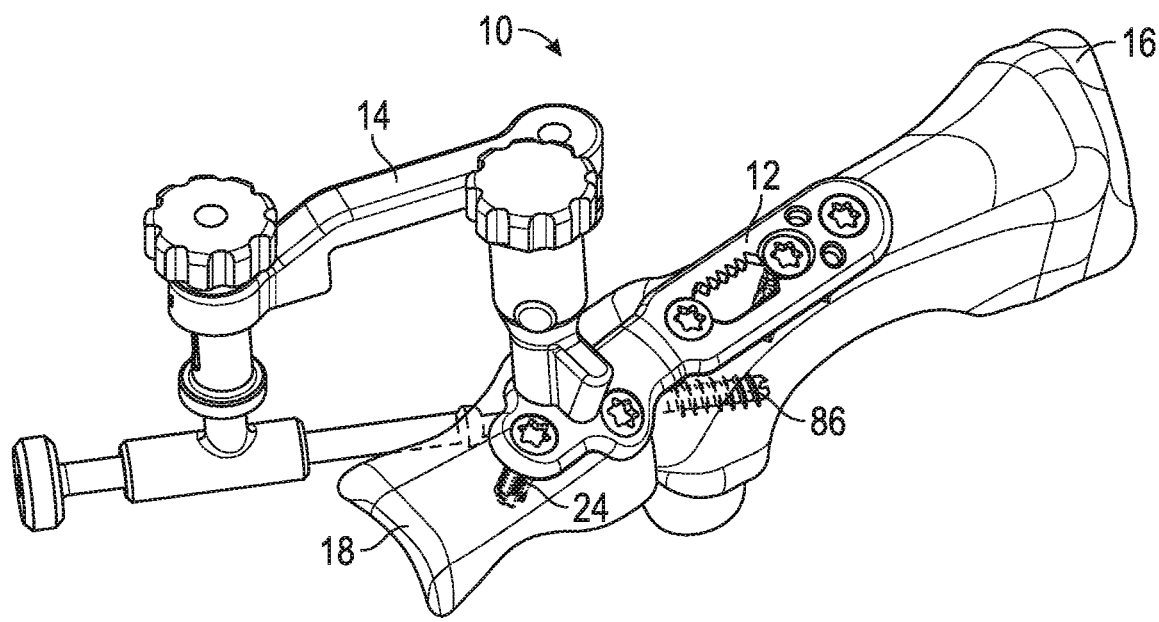
FIG. 1 illustrates a perspective view of an MTP interfragmentary guide and plate system.

An interfragmentary guide and plate system includes a plate and a guide. The plate is attached to a joint. The guide includes a sleeve that can receive a drill or a guide wire. The drill creates a passage in the joint that receives an interfragmentary screw.

Embodiments of the plating system disclosed herein include a bone plate attached to a joint with a plurality of screws. The plating system also includes a guide that includes a sleeve to receive a drill or guide wire. The guide includes a first portion pivotable about a first axis and a second portion pivotable about a second axis. The second portion vertically translates along the second axis. The pivoting and rotation position the sleeve in a desired position to receive the drill or guide wire, and the sleeve defines a plurality of screw trajectories. The drill forms a passage in the joint along one of the plurality of screw trajectories, and the passage receives an interfragmentary screw.

In an embodiment, a plating system includes a metatarsophalangeal (MTP) plate including an aperture and an opening. A locking member is receivable in the aperture to attach the MTP plate to an MTP joint. The plating system includes an MTP guide including a body, an attachment portion, and a rotating portion. The body includes a first end portion and a second end portion that has a passage that receives the rotating portion. The attachment portion is attached to the MTP plate and includes an arm having an end portion. The rotating portion includes at least one dimple and a sleeve to receive a drill or guide wire. The first end portion of the body and the end portion of the arm of the attachment portion are rotationally connected and define a ratcheting mechanism. The ratcheting mechanism allows for rotation of the body, and the body pivots about a first axis to move the sleeve. The rotating portion is rotationally connected to the second end portion of the body of the MTP guide, and the rotating portion pivots about a second axis to move the sleeve. The rotating portion also vertically translates along the second axis and relative to the second end portion of the body to move the sleeve. A sleeve longitudinal axis of the sleeve intersects and is perpendicular to the second axis. The body of the MTP guide includes another opening in communication with the passage of the body, and the another opening has an opening longitudinal axis that intersects and is substantially perpendicular to the second axis of the rotating portion. An another fastener is received in the another opening and spring biased to engage the at least one dimple of the rotating portion and prevent rotation and vertical translation of the rotating portion relative to the body. The attachment portion of the MTP guide is attached to the MTP plate by a fastener that is received in the opening of the MTP plate. One of the MTP plate and the MTP guide includes an alignment pin and the other of the MTP plate and the MTP guide includes a recess, and the alignment pin is received in the recess to prevent rotation of the MTP guide relative to the MTP plate.

In another embodiment, a plating system includes a bone plate including an aperture, and a locking member is receivable in the aperture to attach the bone plate to a joint. The plating system includes a guide including a body, an attachment portion, and a rotating portion. The body includes a first end portion and a second end portion. The attachment portion is attached to the bone plate, and the rotating portion includes a sleeve to receive a drill or guide wire. The first end portion of the body is rotationally connected to the attachment portion and pivots about a first axis to move the sleeve, the rotating portion is rotationally connected to the second end portion of the body of the guide and pivots about a second axis to move the sleeve, the rotating portion translates along the second axis to move the sleeve, and the sleeve defines one of a plurality of trajectories.

In an embodiment, the rotating portion vertically translates along the second axis. In an embodiment, the bone plate includes an opening, and the attachment portion is attached to the bone plate by a fastener that is received in the opening. In an embodiment, at least one of the bone plate and the guide comprise a radiolucent material or partially radiolucent material. In an embodiment, the bone plate comprises carbon fiber, nitinol, polyether ether ketone (PEEK), titanium, stainless steel, or aluminum, and the guide comprises aluminum, PEEK, stainless steel, titanium, or carbon fiber. In an embodiment, one of the bone plate and the guide includes an alignment pin, and the other of the bone plate and the guide includes a recess. The alignment pin is received in the recess to prevent rotation of the guide relative to the bone plate. In an embodiment, the attachment portion includes an arm including an end portion, and the first end portion of the body and the end portion of the arm of the attachment portion are connected. The body rotates relative to the end portion of the arm of the attachment portion about the first axis. In an embodiment, the end portion of the arm of the attachment portion and the first end portion of the body define a ratcheting mechanism that allows for rotation of the body about the first axis. In an embodiment, the second end portion of the body of the guide includes a passage that receives the rotating portion, and the body of the guide includes another opening in communication with the passage of the body. The another opening has an opening longitudinal axis that intersects and is substantially perpendicular to the second axis of the rotating portion. Another fastener is received in the another opening and spring biased to engage the rotating portion to secure the rotating portion and prevent rotation and translation of the rotating portion relative to the body. In an embodiment, the rotating portion includes a translating body extending along the second axis that has an upper end portion and a lower end portion. The translating body includes a plurality of dimples spaced apart along the second axis between the upper end portion and the lower end portion. In an embodiment, an end of the another fastener engages one of the plurality of dimples to secure the rotating portion and prevent rotation and translation of the rotating portion relative to the body of the guide. In an embodiment, the rotating portion includes a translating body extending along the second axis that has an upper end portion and a lower end portion, and the lower end portion of the translating body includes the sleeve that receives the drill or guide wire. A sleeve longitudinal axis of the sleeve intersects and is perpendicular to the second axis. In an embodiment, the sleeve telescopes. In an embodiment, the drill forms a bone passage in a first metatarsal and a proximal phalanx of the joint to receive an interfragmentary screw. In an embodiment, the bone plate is an MTP plate, and the guide is an MTP guide.

In another embodiment, a method for positioning a sleeve that receives a drill or guide wire includes rotating a body of a guide relative to an attachment portion of the guide to pivot the body about a first axis to move a sleeve of a rotating portion of the guide. The attachment portion of the guide is attached to a bone plate. The method includes rotating the rotating portion of the guide relative to the body of the guide to pivot the rotating portion about a second axis to move the sleeve of the rotating portion of the guide. The method includes translating the rotating portion along the second axis relative to the body of the guide to move the sleeve of the rotating portion. The method includes securing the rotating portion relative to the body to secure the sleeve of the rotating portion in a desired location relative to a joint.

In an embodiment, the method includes vertically translating the rotating portion of the guide along the second axis relative to the body of the guide. In an embodiment, the method includes drilling a bone passage in the joint and inserting an intramedullary screw in the bone passage. In an embodiment, the method includes attaching the guide to the bone plate. In an embodiment, the plate is an MTP plate, the bone plate is an MTP plate, and the joint is an MTP joint.

FIG. 1 illustrates an MTP interfragmentary guide and plate system 10 including an MTP plate 12 and an MTP guide 14. The MTP interfragmentary guide and plate system 10 fuses a metatarsophalangeal joint between the first metatarsal 16 and the proximal phalanx 18.

The MTP plate 12 may comprise carbon fiber, nitinol, polyether ether ketone (PEEK), titanium, stainless steel, or aluminum. The MTP guide 14 may comprise aluminum, PEEK, stainless steel, titanium, or carbon fiber. In an embodiment, the MTP plate 12 and/or the MTP guide 14 comprise a radiolucent or partially radiolucent material. In an embodiment, both the MTP plate 12 and the MTP guide 14 are radiolucent. In another embodiment, the MTP guide 14 is radiolucent, and the MTP plate 12 is not radiolucent.

Figure 2:
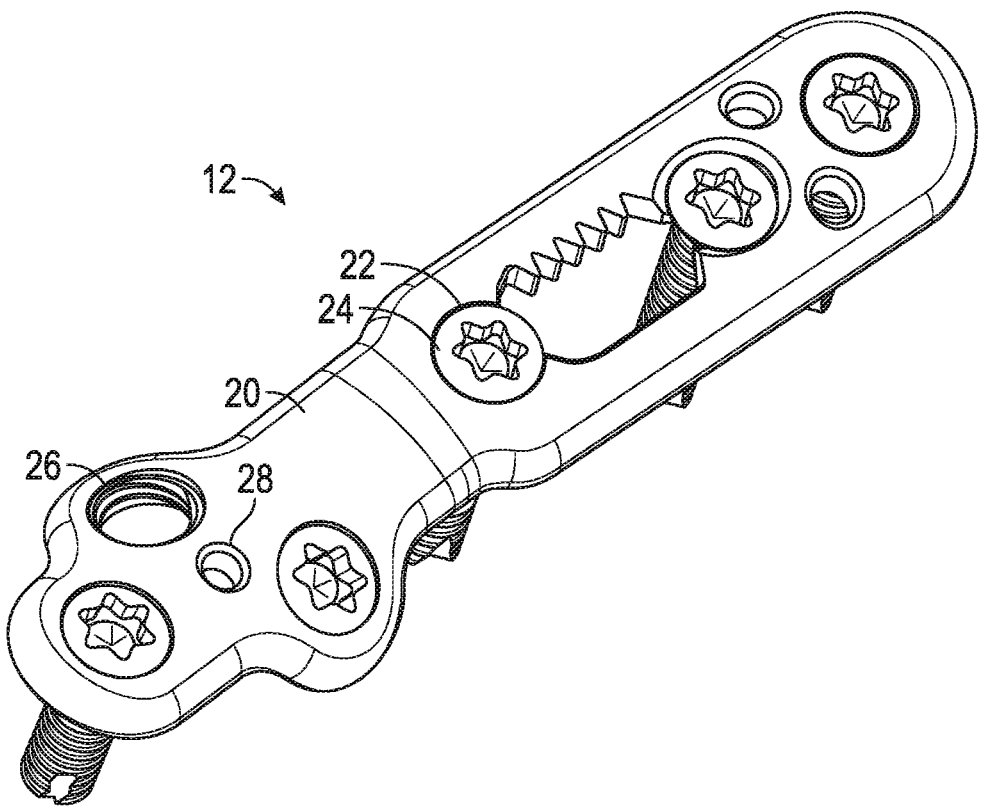
FIG. 2 illustrates a perspective view of an MTP plate.

As illustrated in FIG. 2, the MTP plate 12 includes a body 20 including a plurality of apertures 22 that each receive one threaded locking screw 24. The MTP plate 12 has a curved profile to match the profile of the metatarsophalangeal joint. The MTP plate 12 also includes an opening 26 that receives a fastener 30 of an attachment portion 54 (shown in FIGS. 3 and 4) that attaches the MTP guide 14 to the MTP plate 12 and a mating recess 28 that receives an alignment pin 32 of the attachment portion 54 (shown in FIGS. 3 and 4) to prevent rotation of the MTP guide 14 relative to the MTP plate 12. In another example, the MTP guide 14 includes the mating recess 28, and the MTP plate 12 includes the alignment pin 32.

Figure 3:
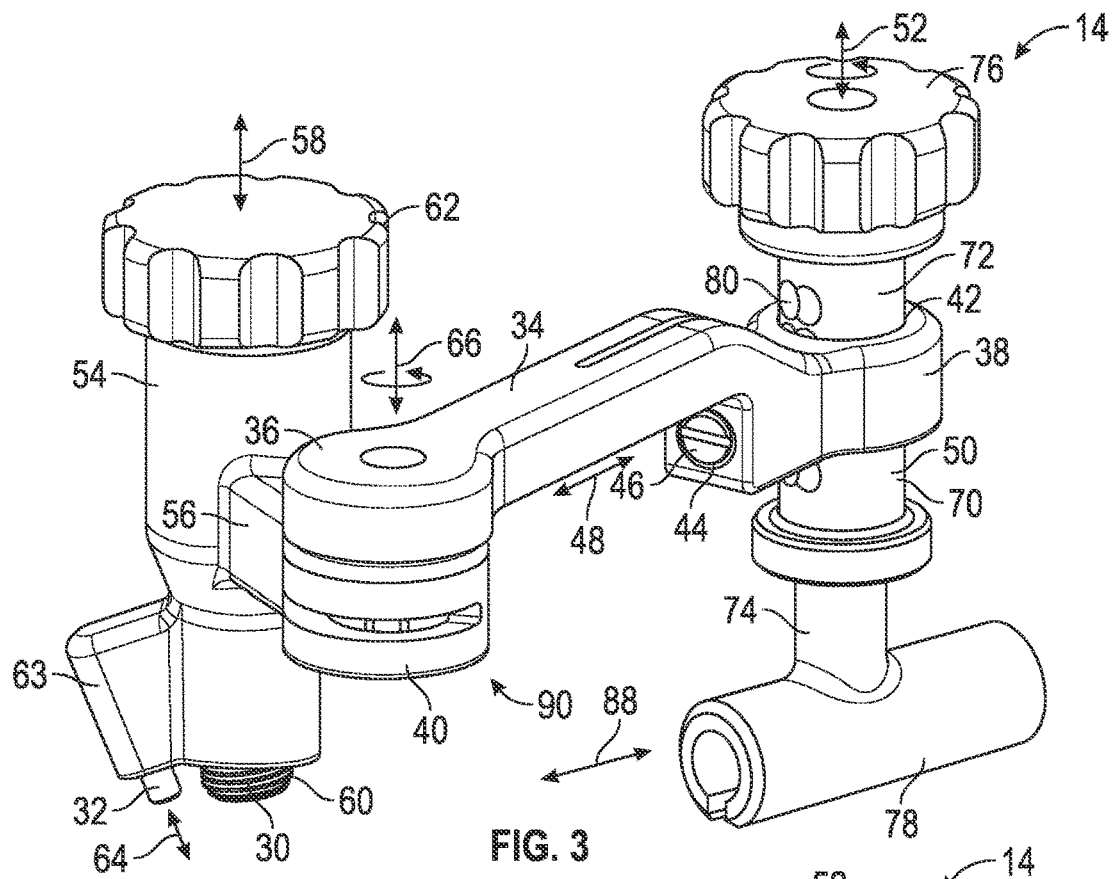
FIG. 3 illustrates a perspective view of an MTP guide.
Figure 4:
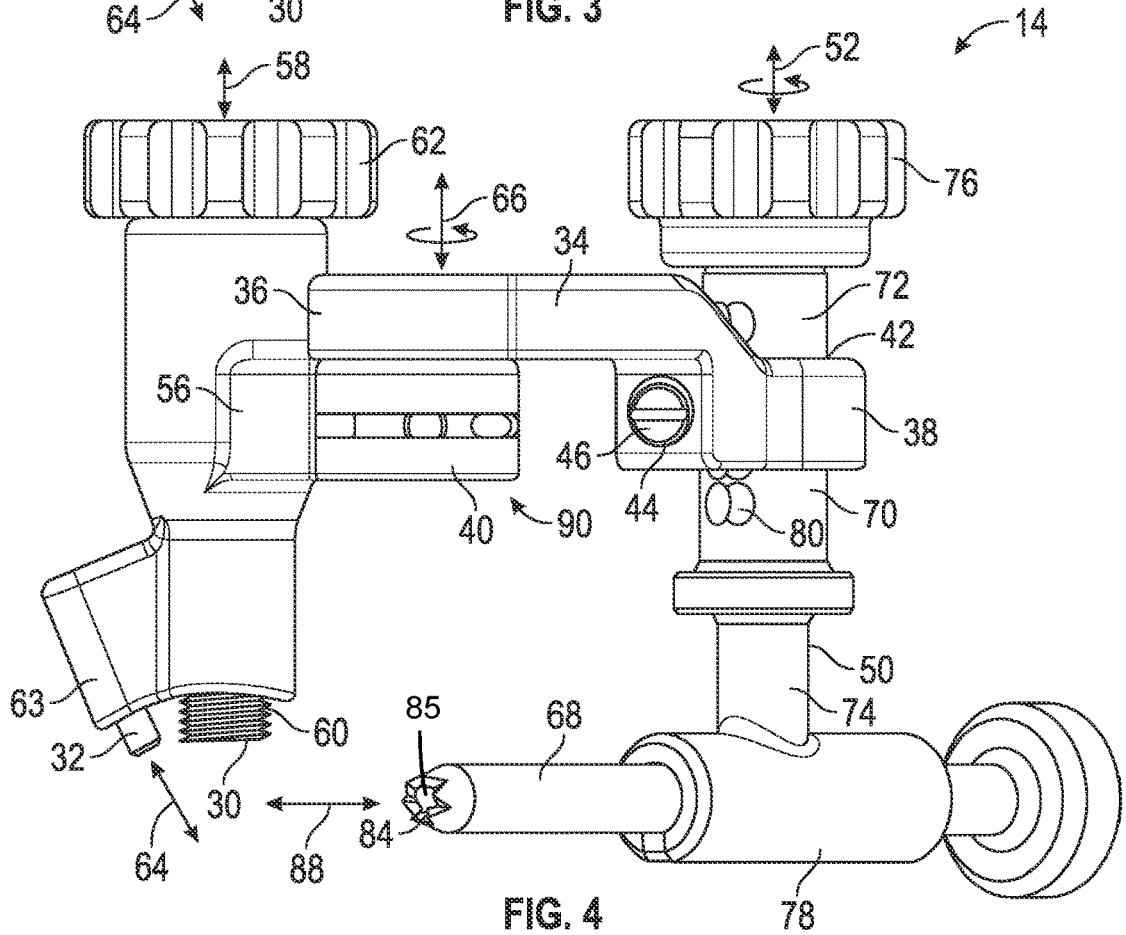
FIG. 4 illustrates a perspective view of the MTP guide and a guide sleeve.

FIGS. 3 and 4 illustrate the MTP guide 14. The MTP guide 14 includes a body 34 having a first end portion 36 and a second end portion 38. The first end portion 36 is rotationally attached to the attachment portion 54 of the MTP guide 14 (described below), and the second end portion 38 includes a passage 42 that receives a rotating portion 50 of the MTP guide 14 (described below).

The body 34 includes an opening 44 in communication with the passage 42 of the second end portion 38. The opening 44 has a longitudinal axis 48 that intersects and is substantially perpendicular to a longitudinal axis 52 of the rotating portion 50. A retaining fastener 46 is received in the opening 44 and biased by a spring (not shown) such that the retaining fastener 46 engages the rotating portion 50 and prevents rotation and vertical translation of the rotating portion 50 relative to the body 34, as described below. The opening 44 can be perpendicular, up to ±5° degrees from perpendicular, up to ±10° degrees from perpendicular, or up to ±15° degrees from perpendicular to the longitudinal axis 52 of the rotating portion 50.

The MTP guide 14 includes the attachment portion 54 that secures the MTP guide 14 to the MTP plate 12. The attachment portion 54 includes an arm 56 including an end portion 40. The attachment portion 54 includes a passage (not shown) that extends along a longitudinal axis 58. The fastener 30 includes a shaft 60 that is received in the passage, and a knob 62 can be turned to position the fastener 30 in the opening 26 of the MTP plate 12 to secure the attachment portion 54 to the MTP plate 12. In one example, the fastener 30 is a threaded fastener, the shaft 60 is a threaded shaft, the opening 26 is a threaded opening, and the passage is a threaded passage. In one example, the fastener 30 is a thumb screw. In another example, the fastener 30 and the opening 26 are not threaded.

The attachment portion 54 also includes a flange 63 including the downwardly extending alignment pin 32 that is received in the mating recess 28 of the MTP plate 12 to prevent rotation of the MTP guide 14 relative to the MTP plate 12. The alignment pin 32 extends along a longitudinal axis 64 that is offset from and intersects the longitudinal axis 58. As stated above, in another example, the MTP guide 14 includes the mating recess 28, and the MTP plate 12 includes the alignment pin 32.

The first end portion 36 of the body 20 and the end portion 40 of the arm 56 of the attachment portion 54 are connected by a ratcheting mechanism 90 that allows the body 34 to rotate relative to the attachment portion 54 about an axis 66. The axis 66 is substantially parallel to the longitudinal axis 58 of the attachment portion 54 and the longitudinal axis 52 of the rotating portion 50. The ratcheting mechanism 90 allows for fine ratcheting when the body 34 is rotated relative to the attachment portion 54 and secures the body 34 relative to the attachment portion 54 to prevent movement of the body 34.

The MTP guide 14 also includes the rotating portion 50 that receives a guide sleeve 68 (shown in FIG. 4). The rotating portion 50 includes a body 70 extending along the longitudinal axis 52 that has an upper end portion 72 and a lower end portion 74. The upper end portion 72 of the body 70 includes a knob 76, and the lower end portion 74 of the body 70 includes a sleeve 78 that receives the guide sleeve 68. The sleeve 78 extends along a longitudinal axis 88 that intersects and is perpendicular to the longitudinal axis 52 of the rotating portion 50. In one example, the guide sleeve 68 telescopes to protect soft tissue in the area of the metatarsophalangeal joint. In another example, the sleeve 78 telescopes to protect soft tissue in the area of the metatarsophalangeal joint. In another example, both the guide sleeve 68 and the sleeve 78 telescope to protect soft tissue in the area of the metatarsophalangeal joint.

The body 70 also includes a plurality of dimples 80 spaced along the longitudinal axis 52 between the upper end portion 72 and the lower end portion 74 at a longitudinal position. In one example, the plurality of dimples 80 are equally spaced along the longitudinal axis 52. In one example, there are two or more dimples 80 at each longitudinal position along the longitudinal axis 52 of the rotating portion 50. In one example, there are dimples 80 at five longitudinal positions along the longitudinal axis 52 of the rotating portion 50, and two dimples 80 at each of the five longitudinal positions along the longitudinal axis 52 of the rotating portion 50. In this example, there are ten dimples 80. However, the rotating portion 50 can include any number of dimples 80 in any configuration.

The body 70 of the rotating portion 50 is received in the passage 42 of the second end 38 of the body 34 of the MTP guide 14. The rotating portion 50 can rotate about the longitudinal axis 52 and vertically translate along the longitudinal axis 52 relative to the body 70. As a result, the sleeve 78 has an infinite number of trajectories. Once the rotating portion 50 is positioned so that the sleeve 78 is in a desired position, the retainer fastener 46 is spring biased within the opening 44 such that an end (not shown) of the retainer fastener 46 is received in one of the dimples 80 on the body 70 of the rotating portion 50, securing the rotating portion 50 relative to the body 34 of the MTP guide 14 to prevent rotation and vertical translation of the rotating portion 50 relative to the body 34. Once the sleeve 78 is in the desired position, the desired trajectory of the interfragmentary screw 86 is also determined.

The MTP plate 12 is positioned on the metatarsophalangeal joint as shown in FIG. 1, and a threaded locking screw 24 is received each of the plurality of apertures 22 to secure the MTP plate 12 to the metatarsophalangeal joint. The MTP guide 14 is then attached to the MTP plate 12. An end of the fastener 30 of the attachment portion 54 of the MTP guide 14 is received in the opening 26 of the MTP plate 12, and the knob 62 of the fastener 30 is rotated to secure the MTP guide 14 to the MTP plate 12. The alignment pin 32 of the attachment portion 54 of the MTP guide 14 is received in the mating recess 28 of the MTP plate 12 to prevent the MTP guide 14 from rotating relative to the MTP plate 12.

The body 34 of the MTP guide 14 can be rotated relative to the attachment portion 54 of the MTP guide 14 about the axis 66 to position the body 34 and the sleeve 78 in a desired position.

The rotating portion 50 and therefore the sleeve 78 is then moved relative to the body 34. The rotating portion 50 is rotated in the passage 42 of the second end portion 38 of the body 34 about the longitudinal axis 52 and vertically translated along the longitudinal axis 52 until the sleeve 78 is in a desired position. The retaining fastener 46 is spring biased in the opening 44 to engage a dimple 80 of the rotating portion 50, securing the rotating portion 50 in a position relative to the body 34.

The sleeve 78 has an infinite number of trajectories. Once the sleeve 78 is in the desired position, the guide sleeve 68 including teeth 84 is positioned in the sleeve 78. The teeth 84 engage bone to help secure the guide sleeve 68 to the bone. The guide sleeve 68 includes a passage 85 that can receive a guide wire, e.g., a K-wire (not shown). The guide sleeve 68 is removed from the sleeve 78, and a drill (not shown) could then be received in the sleeve 78. The drill creates a drilled passage through the metatarsophalangeal joint, and the drill is then removed from the sleeve 78. In another example, no drill is employed. The interfragmentary screw 86 (shown in FIG. 1) is received in the sleeve 78, which positions the interfragmentary screw 86 in the drilled passage in the metatarsophalangeal joint so that the interfragmentary screw 86 enters one of the first metatarsal 16 and the proximal phalanx 18 and exits the other of the first metatarsal 16 and the proximal phalanx 18 in a path that avoids the threaded locking screws 24 that retain the MTP plate 12 to the metatarsophalangeal joint and maximizes bone purchase with the interfragmentary screw 86. The interfragmentary screw 86 can include a passage through which the guide wire or K-wire passes.

The trajectory of the interfragmentary screw 86 can be recommended or customizable based on a specific patient's anatomy. Differences in anatomy can be determined by either fluoroscopy and/or image intensification. The MTP interfragmentary guide and plate system 10 only provides one passage 78 that defines the trajectory of the interfragmentary screw 86, but there are an infinite number of trajectories of the interfragmentary screw 86 possible by rotating portions of the MTP guide 14 about two separate pivot points and vertically translating a portion of the MTP guide 14 with respect to the MTP plate 12.

It should be understood that many additional changes in the details, materials, steps and arrangements of parts, which have been herein described and illustrated in order to explain the nature of the present embodiments, may be made by those skilled in the art while still remaining within the principles and scope of the disclosed embodiments.

What is claimed is:

1. A plating system comprising:
   a metatarsophalangeal (MTP) plate including an aperture and an opening, wherein a locking member is receivable in the aperture to attach the MTP plate to an MTP joint; and
   an MTP guide including a body having a first end portion and a second end portion having a passage that receives a rotating portion, an attachment portion attached to the MTP plate including an arm having an end portion, and the rotating portion including at least one dimple and a sleeve to receive a drill or a guide wire,
   wherein the first end portion of the body and the end portion of the arm of the attachment portion are rotationally connected and define a ratcheting mechanism that allows for rotation of the body such that the body pivots about a first axis to move the sleeve, the rotating portion is rotationally connected to the second end portion of the body such that the rotating portion pivots about a second axis to move the sleeve, the rotating portion vertically translates along the second axis to move the sleeve, and a sleeve longitudinal axis of the sleeve intersects and is perpendicular to the second axis,
   wherein the body includes another opening in communication with the passage of the body, the another opening has an opening longitudinal axis that intersects and is substantially perpendicular to the second axis of the rotating portion, and a fastener is received in the another opening and spring biased to engage the at least one dimple of the rotating portion to prevent rotation and vertical translation of the rotating portion relative to the body,
   wherein the attachment portion of the MTP guide is attached to the MTP plate by a fastener that is received in the opening of the MTP plate, and
   wherein one of the MTP plate and the MTP guide includes an alignment pin and the other of the MTP plate and the MTP guide includes a recess, and the alignment pin is received in the recess to prevent rotation of the MTP guide relative to the MTP plate.

2. A plating system comprising:
   a bone plate including an aperture, wherein a locking member is receivable in the aperture to attach the bone plate to a joint; and
   a guide including a body having a first end portion and a second end portion, an attachment portion attached to the bone plate, and a rotating portion including a sleeve to receive a drill or a guide wire, wherein the first end portion of the body is rotationally connected to the attachment portion to pivot the body about a first axis to move the sleeve, the rotating portion is rotationally connected to the second end portion of the body of the guide to pivot the rotating portion about a second axis to move the sleeve, the rotating portion translates along the second axis to move the sleeve, the sleeve defines one of a plurality of trajectories, and the rotating portion includes a translating body extending along the second axis that has an upper end portion and a lower end portion, the lower end portion of the translating body includes the sleeve that receives the drill or the guide wire, and a sleeve longitudinal axis of the sleeve intersects and is perpendicular to the second axis.

3. The plating system as recited in claim 2, wherein the rotating portion translates vertically along the second axis to move the sleeve.

4. The plating system as recited in claim 2, wherein the bone plate includes an opening, and the attachment portion is attached to the bone plate by a fastener that is received in the opening.

5. The plating system as recited in claim 2, wherein at least one of the bone plate and the guide comprise a radiolucent material or partially radiolucent material.

6. The plating system as recited in claim 2, wherein the bone plate comprises carbon fiber, nitinol, polyether ether ketone (PEEK), titanium, stainless steel, or aluminum, and the guide comprises aluminum, PEEK, stainless steel, titanium, or carbon fiber.

7. The plating system as recited in claim 2, wherein one of the bone plate and the guide includes an alignment pin and the other of the bone plate and the guide includes a recess, and the alignment pin is received in the recess to prevent rotation of the guide relative to the bone plate.

8. The plating system as recited in claim 2, wherein the attachment portion includes an arm including an end portion, the first end portion of the body and the end portion of the arm of the attachment portion are connected, and the body rotates relative to the end portion of the arm of the attachment portion about the first axis.

9. The plating system as recited in claim 2, wherein the sleeve telescopes.

10. The plating system as recited in claim 2, wherein the drill forms a bone passage in a first metatarsal and a proximal phalanx of the joint to receive an interfragmentary screw.

11. The plating system as recited in claim 2, wherein the bone plate is an MTP plate and the guide is an MTP guide.

12. A plating system comprising:
a bone plate including an aperture, wherein a locking member is receivable in the aperture to attach the bone plate to a joint; and
a guide including a body having a first end portion and a second end portion, an attachment portion attached to the bone plate, and a rotating portion including a sleeve to receive a drill or a guide wire, wherein the first end portion of the body is rotationally connected to the attachment portion to pivot the body about a first axis to move the sleeve, the rotating portion is rotationally connected to the second end portion of the body of the guide to pivot the rotating portion about a second axis to move the sleeve, the rotating portion translates along the second axis to move the sleeve, the sleeve defines one of a plurality of trajectories, the attachment portion includes an arm including an end portion, the first end portion of the body and the end portion of the arm of the attachment portion are connected, the body rotates relative to the end portion of the arm of the attachment portion about the first axis, and the end portion of the arm of the attachment portion and the first end portion of the body define a ratcheting mechanism that allows for rotation of the body about the first axis.

13. A plating system comprising:
a bone plate including an aperture, wherein a locking member is receivable in the aperture to attach the bone plate to a joint; and
a guide including a body having a first end portion and a second end portion, an attachment portion attached to the bone plate, and a rotating portion including a sleeve to receive a drill or guide wire, wherein the first end portion of the body is rotationally connected to the attachment portion to pivot the body about a first axis to move the sleeve, the rotating portion is rotationally connected to the second end portion of the body of the guide to pivot the rotating portion about a second axis to move the sleeve, the rotating portion translates along the second axis to move the sleeve, the sleeve defines one of a plurality of trajectories, the second end portion of the body of the guide includes a passage that receives the rotating portion, the body of the guide includes another opening in communication with the passage of the body, the another opening has an opening longitudinal axis, the opening longitudinal axis of the another opening intersects and is substantially perpendicular to the second axis of the rotating portion, and another fastener is received in the another opening and spring biased to engage the rotating portion to secure the rotating portion and prevent rotation and translation of the rotating portion relative to the body of the guide.

14. The plating system as recited in claim 13, wherein the rotating portion includes a translating body extending along the second axis having an upper end portion and a lower end portion, the translating body includes a plurality of dimples spaced apart along the second axis between the upper end portion and the lower end portion.

15. The plating system as recited in claim 14, wherein an end of the another fastener engages one of the plurality of dimples to secure the rotating portion and prevent rotation and translation of the rotating portion relative to the body of the guide.

16. A method for positioning a sleeve that receives a drill or a guide wire comprising:
rotating a body of a guide relative to an attachment portion of the guide to pivot the body about a first axis to move a sleeve of a rotating portion of the guide, wherein the attachment portion of the guide is attached to a bone plate;
rotating the rotating portion of the guide relative to the body of the guide to pivot the rotating portion about a second axis to move the sleeve of the rotating portion of the guide;
translating the rotating portion of the guide along the second axis relative to the body of the guide to move the sleeve of the rotating portion; and
securing the rotating portion relative to the body to secure the sleeve of the rotating portion in a desired location relative to a joint, wherein the bone plate is an MTP plate, the guide is an MTP guide, and the joint is an MTP joint.

17. The method as recited in claim 16, including vertically translating the rotating portion of the guide along the second axis relative to the body of the guide.

18. The method as recited in claim 16, including attaching the guide to the bone plate.

19. A method for positioning a sleeve that receives a drill or a guide wire comprising:
rotating a body of a guide relative to an attachment portion of the guide to pivot the body about a first axis to move a sleeve of a rotating portion of the guide, wherein the attachment portion of the guide is attached to a bone plate;
rotating the rotating portion of the guide relative to the body of the guide to pivot the rotating portion about a second axis to move the sleeve of the rotating portion of the guide;
translating the rotating portion of the guide along the second axis relative to the body of the guide to move the sleeve of the rotating portion;
securing the rotating portion relative to the body to secure the sleeve of the rotating portion in a desired location relative to a joint; and
drilling a bone passage in the joint and inserting an intramedullary screw in the bone passage.

* * * * *